Oct. 15, 1957 M. L. V. VAN ZANTEN Plant Pat. 1,653
AZALEA PLANT
Filed Dec. 27, 1955 2 Sheets-Sheet 1
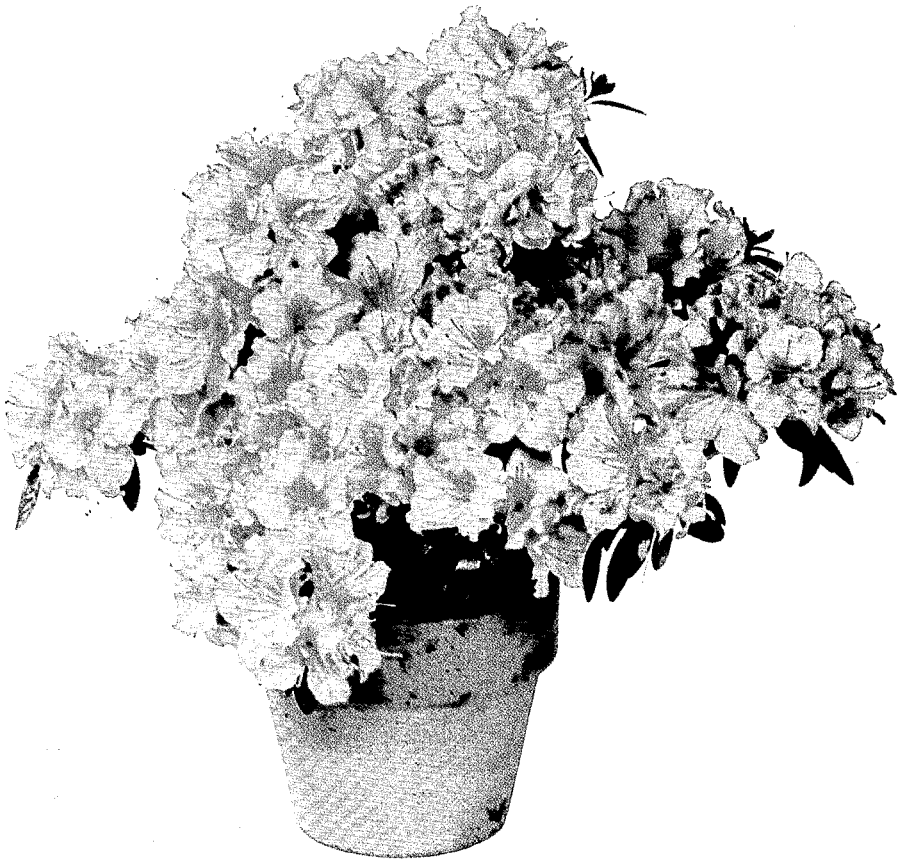
INVENTOR
MAURITS L.V. VAN ZANTEN
BY F. H. Geisler.
ATTORNEY Oct. 15, 1957 M. L. V. VAN ZANTEN Plant Pat. 1,653
AZALEA PLANT
Filed Dec. 27, 1955 2 Sheets-Sheet 2
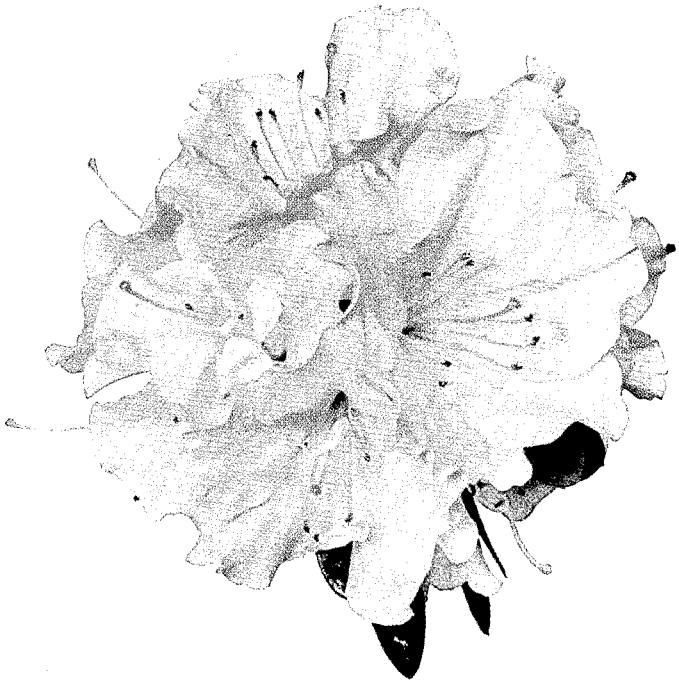
INVENTOR
MAURITS L.V. VAN ZANTEN
BY F. H. Geisler.
ATTORNEY United States Patent Office Plant Pat. 1,653
Patented Oct. 15, 1957

1,653

AZALEA PLANT

Maurits L. V. Van Zanten, Lynden, Wash.

Application December 27, 1955, Serial No. 555,726

1 Claim. (Cl. 47—60)

This invention comprises a new and distinct variety of azalea plant, the result of a cross between a Sander (Hexe) variety, unpatented, and an Indica variety known as "Memoire de Charles Vuylsteke," unpatented, the latter being used as the female plant. The object in making this crossing and in developing this new variety was to produce an improved azalea which would be suitable for early forcing, which would present easy growing characteristics, and which would be free from disease.

Cross pollination was performed under my direction on March 17, 1945, in my greenhouse in Lynden, Washington, and the usual method was followed of hand-pollenizing stigma with pollen of the male plant. The resulting seed was planted in the spring of 1946 and this particular seedling was segregated and retained since it showed remarkable qualities as to foliage, flowering and growing habits, and since it was quite distinct from the particular azalea described in Plant Patent No. 1,233, issued under date of December 15, 1953, which was also developed at the same time.

I took cuttings and studied the behavior of this particular seedling during the following years, and found that these were always constant.

The accompanying illustrations accurately show one of these plants in bloom and also a close-up view of the flowers.

The following is a detailed description of the plant and its flowers:

*Form.*—This new variety is similar to the azalea described in the above mentioned Plant Patent No. 1,233, except that it is more compact and more bushy.

*Foliage.*—The foliage is medium large, oval shaped, about 1½ inches long and ¾ inch wide at the widest part. The color of the top side of the foliage is Ivy Green (Horticultural Color Chart 0001060/3, page 200). The underside is Willow Green (Horticultural Color Chart 000862/1, page 199). The individual leaves are compactly assembled, especially around the terminal ends of the branches, giving the plant the appearance of a well grown miniature rhododendron, and in this respect the plant is quite distinct from any other azalea. The leaves are larger than the leaves of the azalea in Plant Patent No, 1,233 and the foliage and stems are of a stronger tissue.

*Flower buds.*—The flower buds appear in clusters, each cluster comprising five to ten heavy buds, and sometimes there are even as many as eighteen buds in a cluster. This causes the plant to have a very floriferous appearance when in flower and to resemble very much a rhododendron, and this is a distinct and unusual characteristic of the plant. Bud formation takes place very early in the season, usually in July or early August. This plant has a stronger tendency to form flower buds than the plant in Plant Patent No. 1,233. If the plant is pinched back as late as June, it will break again and form well developed buds. Sometimes it is necessary to remove some of the buds during the forcing season, if extra large flowers are desired.

*Flowers.*—The flowers are an intense and distinct bright cherry red color (Horticultural Color Chart 7–22–3, page 157), with a darker center, and are quite distinct in color from the flowers on the azalea plant of Patent No. 1,233 which are claret rose in color. The individual flowers measure from 2¾ to 3 inches across and thus are considerably larger than the flowers in the azalea plant of Patent No. 1,233, and the flowers of the parent plant, Hexe. The flowers are ten-petaled and have distinctly ruffled edges. The flower is hose-in-hose as a result of a petaloid calyx. The size of the petals is 1¾ to 2 inches high and about 1⅜ inches wide. The lower half of each petal shows a dark blotch and the lower part of each petal is grown together with the lower part of the next petal, which is a characteristic of Sander Azalea types. The color of stamens and stigma is cherry red, and there are seven stamens for each flower.

*Characteristics of growth and blooming.*—This plant under forcing grows considerably faster than the azalea plant of Patent No. 1,233 and develops very evenly, giving the entire plant a very rounded and robust appearance. The plant can be forced earlier than the plant of Patent No. 1,233 since it has a tendency to form flower buds earlier in the season. On account of the strong tissue of the foliage the plant can be kept very easily for later forcing if so desired since there is no noticeable loss or drop of leaves. The plant can be forced from early December on, under normal greenhouse conditions, and also can be used very profitably for later forcing if kept cooler. The plant roots very easily and strongly.

This new variety can be grown in the open during the hot summer months without special protection, such as laths or cloth, and, when exposed to full sunlight, the plant takes on a bronze green appearance, whereas the foliage in the azalea of Patent No. 1,233 retains a more light green color when exposed to full sunlight.

Having thus disclosed my invention, I claim:

The new and distinct variety of azalea plant substantially as herein disclosed, characterized particularly by its early blooming and forcing qualities, its compact and bushy form, its large clusters of buds, its large and profuse flowers of cherry red color, and its strong growth.

No references cited.